(12) United States Patent
Sherwood et al.

(10) Patent No.: US 10,933,246 B2
(45) Date of Patent: Mar. 2, 2021

(54) INFECTION FIGHTING BIORESORBABLE POLYMER DEVICE FOR MEDICAL IMPLANTS

(71) Applicant: Cardiac Pacemakers, Inc., St. Paul, MN (US)

(72) Inventors: Gregory J. Sherwood, North Oaks, MN (US); Mary M. Byron, Roseville, MN (US); David R. Wulfman, Minneapolis, MN (US)

(73) Assignee: Cardiac Pacemakers, Inc., St Paul (MN)

( * ) Notice: Subject to any disclaimer, the term of this patent is extended or adjusted under 35 U.S.C. 154(b) by 31 days.

(21) Appl. No.: 16/269,845

(22) Filed: Feb. 7, 2019

(65) Prior Publication Data
US 2019/0184158 A1    Jun. 20, 2019

Related U.S. Application Data

(62) Division of application No. 15/185,398, filed on Jun. 17, 2016, now abandoned.
(Continued)

(51) Int. Cl.
*A61N 1/00* (2006.01)
*A61N 1/375* (2006.01)
(Continued)

(52) U.S. Cl.
CPC .............. *A61N 1/375* (2013.01); *A61L 29/06* (2013.01); *A61L 29/146* (2013.01);
(Continued)

(58) Field of Classification Search
CPC ........ A61N 1/375; A61N 1/3968; A61N 1/05; A61N 1/3629; A61N 1/37512; A61N 1/36;
(Continued)

(56) References Cited

U.S. PATENT DOCUMENTS

| 5,067,491 A | 11/1991 | Taylor et al. |
| 6,530,951 B1 | 3/2003 | Bates et al. |

(Continued)

FOREIGN PATENT DOCUMENTS

| CN | 101332311 A | 12/2008 |
| CN | 101461982 A | 6/2009 |

(Continued)

OTHER PUBLICATIONS

Golda et al, "Oxygen plasma functionalization of parylene C coating for implants surface: Nanotopography and active sites for drug anchoring", Materials Science and Engineering C 33 (2013) 4221-4227.

(Continued)

*Primary Examiner* — Mallika D Fairchild
(74) *Attorney, Agent, or Firm* — Faegre Drinker Biddle & Reath, LLP (57) ABSTRACT

A method of preventing infection resulting from implanting a medical device. The method includes installing a polymer device at least substantially within a subcutaneous pocket formed to contain a housing of the medical device, and installing the medical device housing in the subcutaneous pocket. The polymer device includes a bioresorbable polymer structure and an antimicrobial agent configured to elute from the polymer structure. The polymer device covers less than about 20% of the surface area of the medical device housing.

13 Claims, 5 Drawing Sheets

Related U.S. Application Data (60) Provisional application No. 62/181,570, filed on Jun. 18, 2015.

(51) Int. Cl.

| | | |
|---|---|---|
| *A61N 1/05* | (2006.01) | |
| *A61L 31/14* | (2006.01) | |
| *A61L 31/16* | (2006.01) | |
| *A61L 29/06* | (2006.01) | |
| *A61L 29/14* | (2006.01) | |
| *A61L 29/16* | (2006.01) | |
| *A61L 31/06* | (2006.01) | |
| *A61M 5/142* | (2006.01) | |
| *A61N 1/39* | (2006.01) | |
| *A61N 1/362* | (2006.01) | |

(52) U.S. Cl.
CPC .............. *A61L 29/148* (2013.01); *A61L 29/16* (2013.01); *A61L 31/06* (2013.01); *A61L 31/146* (2013.01); *A61L 31/148* (2013.01); *A61L 31/16* (2013.01); *A61M 5/14276* (2013.01); *A61N 1/05* (2013.01); *A61N 1/3968* (2013.01); *A61L 2300/404* (2013.01); *A61L 2300/604* (2013.01); *A61N 1/3629* (2017.08); *A61N 1/37512* (2017.08)

(58) Field of Classification Search
CPC ....... A61N 1/362; A61L 29/06; A61L 29/146; A61L 29/148; A61L 29/16; A61L 31/146; A61L 31/06; A61L 31/148; A61L 2300/404; A61L 2300/604; A61M 5/14276

See application file for complete search history.

(56) References Cited

U.S. PATENT DOCUMENTS

| | | | |
|---|---|---|---|
| 7,529,592 | B2 | 5/2009 | Cates et al. |
| 7,947,301 | B2 | 5/2011 | Bischoff et al. |
| 8,282,911 | B2 | 10/2012 | Stark et al. |
| 8,315,700 | B2 | 11/2012 | Citron et al. |
| 8,388,994 | B1 | 3/2013 | Scheer et al. |
| 8,591,531 | B2 | 11/2013 | Buevich et al. |
| 8,927,004 | B1 | 1/2015 | Dehnad et al. |
| 10,039,862 | B2 | 8/2018 | Frankson et al. |
| 2003/0083646 | A1 | 5/2003 | Sirhan et al. |
| 2004/0230273 | A1 | 11/2004 | Cates et al. |
| 2006/0141015 | A1 | 6/2006 | Tessier et al. |
| 2007/0098806 | A1 | 5/2007 | Ismail et al. |
| 2008/0051872 | A1 | 2/2008 | Borck |
| 2008/0128315 | A1 | 6/2008 | Buevich et al. |
| 2008/0132922 | A1 | 6/2008 | Buevich et al. |
| 2008/0260796 | A1 | 10/2008 | Bischoff et al. |
| 2009/0024097 | A1 | 1/2009 | Okoniewski |
| 2009/0053278 | A1 | 2/2009 | Fatora et al. |
| 2010/0098744 | A1 | 4/2010 | Ferris et al. |
| 2010/0168808 | A1 | 7/2010 | Citron |
| 2010/0196440 | A1 | 8/2010 | Stark et al. |
| 2011/0038131 | A1 | 2/2011 | Hogg et al. |
| 2012/0121657 | A1 | 5/2012 | Zhou et al. |
| 2013/0011456 | A1 | 1/2013 | Kumar et al. |
| 2013/0018448 | A1 | 1/2013 | Folan et al. |
| 2013/0144356 | A1 | 6/2013 | Horn et al. |
| 2013/0177504 | A1 | 7/2013 | Macoviak |
| 2014/0220098 | A1 | 8/2014 | Lerner et al. |
| 2015/0086604 | A1 | 3/2015 | Buevich et al. |
| 2016/0367800 | A1 | 12/2016 | Sherwood et al. |
| 2017/0007744 | A1 | 1/2017 | Frankson et al. |

FOREIGN PATENT DOCUMENTS

| | | | |
|---|---|---|---|
| CN | 102365102 A | | 2/2012 |
| DE | 102009007667 A1 | | 8/2010 |
| EP | 0968013 B1 | | 10/2005 |
| EP | 2099370 A2 | | 9/2009 |
| EP | 2079389 B1 | | 1/2018 |
| JP | 10-263087 A | | 10/1998 |
| JP | 2001-512354 A | | 8/2001 |
| JP | 2005-507708 A | | 3/2005 |
| JP | 2007-507278 A | | 3/2007 |
| JP | 2009-039522 A | | 2/2009 |
| JP | 2010-508914 A | | 3/2010 |
| JP | 2012-517284 A | | 8/2012 |
| JP | 2014-524980 A | | 9/2014 |
| WO | 2005/032400 A2 | | 4/2005 |
| WO | 2008/071330 A2 | | 6/2008 |
| WO | 2011/127478 A1 | | 10/2011 |
| WO | 2013/191760 A1 | | 12/2013 |

OTHER PUBLICATIONS

Gorham, William F., A New, General Synthetic Method for the Preparation of Linear Poly-p-xylylenes, Journal of Polymer Science: Part A-1, Jan. 1, 1966, pp. 3027-3039.

Grinberg, Olga, et al. "Antibiotic Nanoparticles Embedded Into the Parylene C Layer as a New Method to Prevent Medical Device-Asociated Infections." J. Mater. Chem. B, 3:59-64, 2015.

H1465, Implantable Lead Infection Barrier. Jul. 4, 1995. Stokes, et. al. 4 pages.

Hasan, Mahabub, et al Application of Electrospinning Techniques for tile Production of Tissue Engineering Scaffolds: A Review, European Scientific Journal, 10(15): 265-278, May 2014.

International Search Report and Written Opinion issued in PCT/US2016/038032, dated Sep. 9, 2016, 12 pages.

International Search Report and Written Opinion issued in PCT/US2016/041572 dated Sep. 29, 2016, 13 pages.

Khalil, Abdelrazek Khalil, et al. Preparation and Characterization of Electrospun PLGA/silver Composite Nanofibers for Biomedical Applications. International Journal of Electrochemical Science, 8:3483-3493, 2013.

Kumar, Rakesh. New Technology Offers Alternative Antimicrobial Solution [Online]. Medical Design, Feb. 14, 2014, pages., [retrieved on Apr. 16, 20151 Retrieved from http://medicaldesign.com/print/materials/new-technology-offers-alternative-antimicrobial-solution.

Maggioni et al., An Innovative Pathway towards Nano-Sized Parylene-Based Materials Prepared by Plasma-Based Deposition: Example of Application to the Production of Antimicrobial Materials, Plasma Process. Polym. Mar. 21, 2014, 11, Wiley-VCH Verlag GmbH & Co. KGaA, Weinheim, wileyonlinelibrary.com. pp. 489-495.

Wang, Heran, et al., Preparation and Optimizatin of Silver Nanoparticles Embeddded Electrospun Membrane for Implant Associated Infections Prevention. American Chemical Society, Applied Materials & Interfaces: 5:11014-11021 2013.

INFECTION FIGHTING BIORESORBABLE POLYMER DEVICE FOR MEDICAL IMPLANTS

CROSS-REFERENCE TO RELATED APPLICATION

This application is a division of U.S. application Ser. No. 15/185,398, filed Jun. 17, 2016, which claims priority to Provisional Application No. 62/181,570, filed Jun. 18, 2015, which is herein incorporated by reference in its entirety.

TECHNICAL FIELD

The present invention relates to preventing infections associated with implantable medical devices. More specifically, the invention relates to devices and methods for delivering antimicrobial agents to a subcutaneous pocket to prevent infections.

BACKGROUND

Implantable medical devices may include a housing and a lead or catheter for delivering therapy to a treatment site within a patient's body. For example, a pacemaker may include a housing, or pulse generator, containing electronics and a battery; and an electrical lead extending from the pulse generator to a treatment site—the heart. In another example, a drug delivery system may include a housing, or drug delivery pump, containing the pump, a battery, and a supply of the drug; and a catheter extending from the drug delivery pump to the treatment site requiring the drug. In some cases, the housing may be installed in a subcutaneous pocket within a patient's body.

Implanting a medical device in a subcutaneous pocket within a patient inherently exposes the patient to a risk of a nosocomial (e.g., hospital-acquired) infection. For example, the average nosocomial infection rate associated with the implantation of pacemakers and implantable cardioverter defibrillators is approximately 3%. In some cases of infection, the implantable medical device, including a device housing and any associated electrical leads or catheters, must be completely removed. Following removal, the infection must be cured and the patient must heal enough to tolerate implantation of a replacement medical device. The costs of such infections are significant, not only intrinsically, but also in terms of the physical and emotional stress suffered by the patient.

What is needed is a way to prevent infections which may result from implanting a medical device in a subcutaneous pocket without interfering in the operation of the medical device.

SUMMARY

Example 1 is a method of preventing infection resulting from implanting a medical device. The method includes installing a polymer device at least substantially within a subcutaneous pocket formed to contain a housing of the medical device, and installing the medical device housing in the subcutaneous pocket. The polymer device includes a bioresorbable polymer structure and an antimicrobial agent configured to elute from the polymer structure. The polymer device covers less than about 20% of the surface area of the medical device housing.

Example 2 is the method of Example 1, wherein the antimicrobial agent elutes from the polymer structure as the polymer structure is bioresorbed.

Example 3 is the method of either of Examples 1 or 2, wherein the polymer device has a tubular shape and installing the polymer device includes passing at least one electrical lead or at least one catheter through the polymer device, and connecting the at least one electrical lead or the at least one catheter to the housing of the medical device such that the lead or catheter extends from the implantable medical device housing to a treatment site.

Example 4 is the method of Example 3, wherein installing the polymer device further includes adjusting a position of the polymer device along the at least one electrical lead or at least one catheter such that an end of the polymer device is adjacent to or within a blood vessel through which the lead or catheter passes.

Example 5 is the method of either of Examples 1 or 2, wherein the polymer device is formed as a polymer tape, and installing the polymer device includes wrapping at least one electrical lead or at least one catheter with the polymer tape to form a tubular shape around the at least one electrical lead or at least one catheter, and connecting the at least one electrical lead or the at least one catheter to the housing of the medical device so that the lead or catheter extends from the implantable medical device housing to a treatment site.

Example 6 is the method of Example 5, wherein the polymer device is installed such that an end of the polymer device is adjacent to or within a blood vessel through which the lead or catheter passes.

Example 7 is the method of either of Examples 1 or 2, wherein installing the polymer device includes fitting the polymer device around a substantial portion of a perimeter of the subcutaneous pocket.

Example 8 is the method of Example 7, wherein the polymer device is fitted around at least 50% of a length of the perimeter of the subcutaneous pocket.

Example 9 is the method of Example 7, wherein the polymer device is fitted around at least 90% of a length of the perimeter of the subcutaneous pocket.

Example 10 is the method of Example 7, wherein the polymer device is fitted around 100% of a length of the perimeter of the subcutaneous pocket.

Example 11 is the method of Example 1, wherein the antimicrobial agent is configured to elute from the bioresorbable polymer structure independently of the bioresorbtion of the bioresorbable polymer structure.

Example 12 is the method of any of Examples 1-11, wherein the medical device is an implantable cardioverter-defibrillator.

Example 13 is a method of preventing infection resulting from implanting a medical device. The method includes implanting a polymer device at least substantially within a subcutaneous pocket formed to contain a housing of the medical device, implanting the medical device housing in the subcutaneous pocket, and adjusting a position of the polymer device along the at least one electrical lead or at least one catheter such that an end of the polymer device is adjacent to or within a blood vessel through which the at least one electrical lead or at least one catheter passes. The polymer device includes a bioresorbable polymer structure and an antimicrobial agent configured to elute from the polymer structure. The medical device including at least one electrical lead or at least one catheter.

Example 14 is the method of claim 13, wherein the end of the polymer device is within the blood vessel and polymer device is substantially within the subcutaneous pocket.

Example 15 is the method of claim 13, wherein the end of the polymer device is within the blood vessel and at least 80% of the polymer device is within the subcutaneous pocket.

Example 16 is the method of claim 13, wherein the polymer device is entirely within the subcutaneous pocket and an end of the polymer device is adjacent to the blood vessel.

Example 17 is the method of any of claims 13-16, wherein implanting the polymer device further includes passing at least one electrical lead or at least one catheter through the polymer device, and connecting the at least one electrical lead or the at least one catheter to the housing of the medical device such that the lead or catheter extends from the implantable medical device housing to a treatment site.

Example 18 is the method of any of claims 13-16, wherein implanting the polymer device further includes wrapping at least one electrical lead or at least one catheter with the polymer tape to form a tubular shape around the at least one electrical lead or at least one catheter, and connecting the at least one electrical lead or the at least one catheter to the housing of the medical device so that the lead or catheter extends from the implantable medical device housing to a treatment site.

Example 19 is the method of any of claims 13-18, wherein the antimicrobial agent is configured to elute from the bioresorbable polymer structure independently of the bioresorbtion of the bioresorbable polymer structure.

Example 20 is the method of any of claims 13-18, wherein the antimicrobial agent is configured to elute along with the bioresorbtion of the bioresorbable polymer structure.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
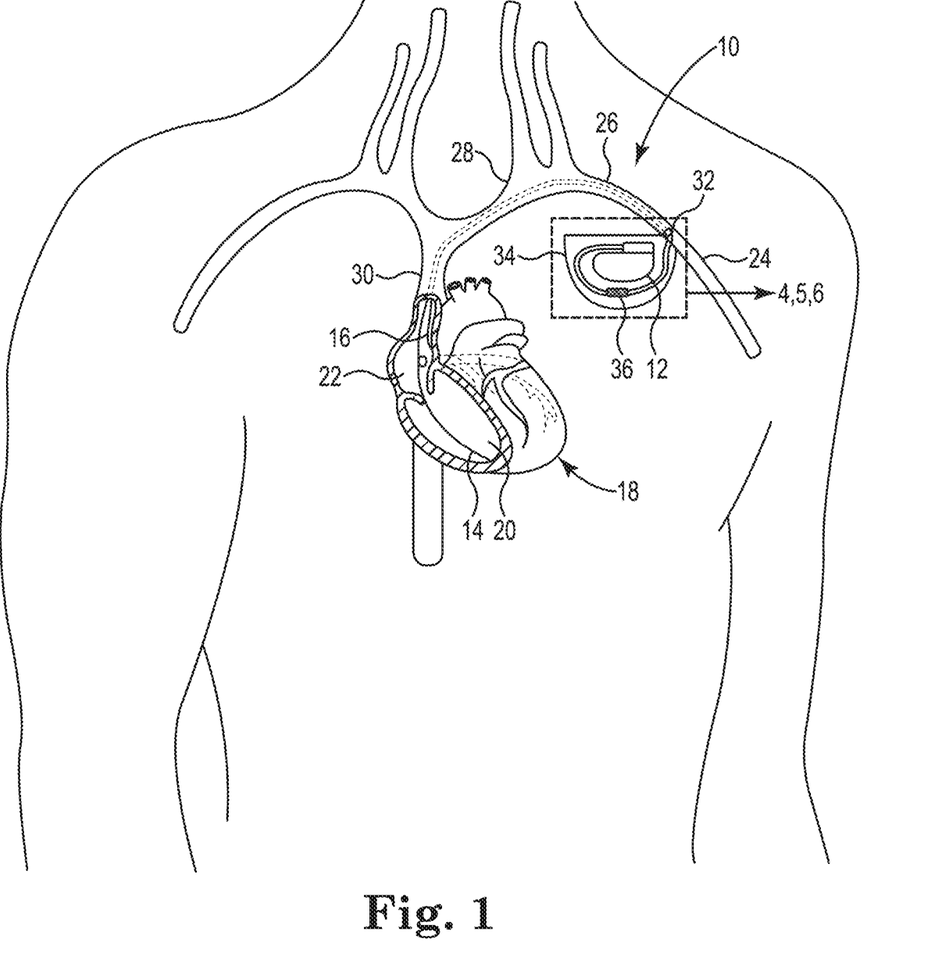
FIG. 1 is a schematic view of an implantable medical device subcutaneously implanted within a patient in accordance with embodiments of the present invention.

FIG. 1 provides an illustrative but non-limiting example of a medical application using an implantable medical device and a polymer device implanted into a subcutaneous pocket to prevent infection. The application and location are illustrative only, as implantable medical devices incorporating embodiments of the present invention may be used in a variety of anatomical locations and for a variety of additional purposes.

FIG. 1 is a schematic view of an implantable medical device in accordance with embodiments of the present invention. FIG. 1 illustrates an exemplary implantable medical device (IMD) 10 in the form of a cardiac rhythm management system. As shown in FIG. 1, the IMD 10 may include housing 12 and a plurality of leads 14, 16 connecting the housing 12 with treatment sites within a patient's heart 18. The housing 12 may be, for example, a pacemaker or pulse generator, and may include electronic circuitry (not shown) and a battery (not shown). The leads 14, 16 may include conductors and electrodes (not shown) as necessary to convey electrical pulses and signals between the housing 12 and the heart 18. As shown in FIG. 1, the heart 18 includes a right ventricle 20 and a right atrium 22. A major series of veins supplying blood to the heart 18 includes a left auxiliary vein 24, which flows into a left subclavian vein 26, which flows into a left brachiocephalic vein 28. The left brachiocephalic vein 28 flows into a superior vena cava 30, which supplies blood to the right atrium 22.

As further shown in FIG. 1, the plurality of leads 14, 16 may enter the vascular system through a vascular entry site 32. In some embodiments, the vascular entry site 32 may be formed in a wall of the left auxiliary vein 24. In other embodiments, the vascular entry site 32 may be formed in a wall of the left subclavian vein 26. The plurality of leads 14, 16 may extend from the left auxiliary vein 24, through the left subclavian vein 26, the left brachiocephalic vein 28, and the superior vena cava 30 to the heart 18. Within the heart 18, the lead 14 may be implanted in the right ventricle 20 and the lead 16 may be implanted in the right atrium 22. Thus, the right ventricle 20 and the right atrium 22 are treatment sites within the heart 18 that receive therapy from IMD 10 in the form of electrical pulses conveyed from the housing 12 by way of the leads 14, 16. In some embodiments, the housing 12 may require electrical grounding to tissue surrounding the subcutaneous pocket 34 to successfully provide therapy.

The housing 12 may be implanted in a subcutaneous pocket 34 in a patient's chest, as shown in FIG. 1 for example. A portion of the leads 14, 16 extending from the housing 12 to the vascular entry site 32 may also be located within the subcutaneous pocket 34. Any excess length of the leads 14, 16 may be coiled about the housing 12 within the subcutaneous pocket 34.

As shown in FIG. 1, IMD 10 may also include a polymer device 36 implanted within the subcutaneous pocket 34 to prevent infection resulting from implanting the IMD 10, as described below. The polymer device 36 may include a structure made of a bioresorbable polymer and an antimicrobial agent. In some embodiments, the bioresorbable polymer may include poly(lactic-co-glycolic) acid, polycaprolactone (PCL), poly-L-lactide (PLLA), or poly(lactide-co-glycolide)-block-poly(ethylene glycol) (PLGA-b-PEG), or any combination of the aforementioned polymers. In some embodiments, the polymer device 36 may be completely bioresorbable. As used herein, a bioresorbable polymer is a polymer that may be broken down by biological systems to such an extent that it may be completely eliminated from the body. This is in contrast to a bioabsorbable polymer which is a polymer that may be broken down by biological systems, but not necessarily to the extent that it may be completely eliminated from the body.

The antimicrobial agent may be configured to elute from the structure of the polymer device 36. In some embodiments, the antimicrobial agent may be disposed within the bioresorbable polymer. That is, the antimicrobial agent may be integrated into the bioresorbable polymer itself such that as the bioresorbable polymer is broken down, the antimicrobial agent may be released. For example, if the antimicrobial agent is a silver salt mixed into the bioresorbable polymer prior to forming the polymer device 36, silver ions may be released as the bioresorbable polymer is broken down. In some embodiments, the antimicrobial agent may include a silver salt, such as silver nitrate, or silver chloride. In other embodiments, the antimicrobial agent may include silver nanoparticles. In still other embodiments, the antimicrobial agent may include salts or nanoparticles of other metals having antimicrobial properties, such as gold or copper. In such embodiments, the antimicrobial agent may elute from the bioresorbable polymer device 36 as the bioresorbable polymer is bioresorbed.

In other embodiments, the structure of the polymer device 36 may include a plurality of fibers formed of the bioresorbable polymer. The antimicrobial agent may be disposed within spaces formed by the plurality of fibers. In such embodiments, the antimicrobial agent may be supplied as solids within the spaces, solutions within the spaces, emulsions within the spaces, or suspensions within the spaces. The antimicrobial agent may include any antibiotic or combination of antibiotics known in the art, for example, vancomycin, minocycline, gentamycin, or rifampin, or any of the antimicrobial agents described above. In some embodiments, the antimicrobial agent may elute from the spaces between the fibers substantially completely before the bioresorbable polymer device 36 is substantially bioresorbed. For example, the antimicrobial agent may elute substantially completely in a few days, whereas the bioresorbable polymer device 36 may not be substantially bioresorbed for several weeks. In other embodiments, the antimicrobial agent may elute from the spaces of the bioresorbable polymer device 36 in rough proportion to the bioresorbtion of the bioresorbable polymer device 36. For example, the antimicrobial agent may elute substantially completely in a few days, and the bioresorbable polymer device 36 may also be substantially bioresorbed in a few days.

Although FIG. 1 illustrates the exemplary IMD 10 in the form of a subcutaneously-implanted pacemaker housing and lead system, the various embodiments can be implemented in any implantable medical device implanted in a subcutaneous pocket for sensing intrinsic physiological electrical activity, delivering a therapeutic stimulus to patient tissue, or providing other therapy to specific treatment sites. For example, embodiments may be employed with a subcutaneously-implanted implantable cardioverter-defibrillator (ICD) housing and lead system. Such a system may include a housing implanted in a subcutaneous pocket in a patient's chest, and a lead traversing a subcutaneous path from the subcutaneous pocket to the anterior precordial region. Embodiments may be employed within the subcutaneous pocket containing the ICD housing and along the subcutaneous path traversed by the lead. Other such implantable medical devices include, without limitation, cardioverter-defibrillator or cardiac resynchronization therapy devices, leadless pacing devices, endocardial leads, epicardial leads, neurostimulation systems such as spinal cord stimulation or deep brain stimulation device housings and associated leads, and implantable drug pumps, to name a few.

Figure 2:
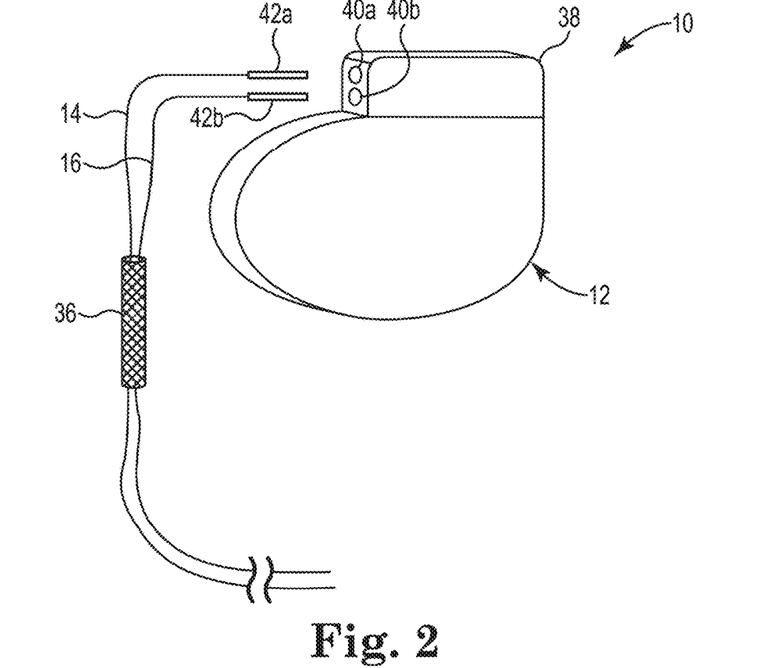
FIG. 2 is a schematic view of the implantable medical device of FIG. 1 including a polymer device in accordance with embodiments of the present invention.

FIG. 2 is a schematic view of the IMD 10 of FIG. 1 including the polymer device 36 in accordance with embodiments of the present invention. As shown in FIG. 2, the IMD 10 may further include a header 38 connected to the housing 12. The header 38 may include a plurality of terminal pin receiving ports 40a, 40b, that are electrically connected to the electronic circuitry (not shown) within the housing 12. The leads 14, 16 may include a plurality of terminal pins 42a, 42b. The terminal pins 42a, 42b may be inserted into the terminal pin receiving ports 40a, 40b to connect the leads 14, 16 to the housing 12. As shown in FIG. 2, the polymer device 36 may have a tubular shape that fits around the leads 14, 16 as they pass through the polymer device 36. In some embodiments, the polymer structure may be elastic and formed such that the polymer device 36 fits tightly around the leads 14, 16 so that the polymer device 36 is not likely to move along the leads 14, 16 without an effort by the surgeon to do so. In some embodiments, the surgeon may move the polymer device 36 along the leads 14, 16 to position the polymer device 36 as desired for a particular patient. The ability of the surgeon to achieve a position the polymer device 36 as desired for a particular patient may lead to a more successful outcome in terms of infection prevention and patient comfort. In some embodiments, the polymer device 36 may be flexible to further facilitate the ability of the surgeon to achieve the position the polymer device 36 as desired for a particular patient.

In some embodiments, the polymer device 36 may be formed by extruding the bioresorbable polymer structure and the antimicrobial agent together to form an elongated shape having a hollow opening extending axially the length of the polymer device 36. In some embodiments, the polymer device 36 may have a tubular shape. In other embodiments, the polymer device 36 may be formed by molding the bioresorbable polymer structure and the antimicrobial agent together to form an elongated shape having a hollow opening extending axially the length of the polymer device 36. In other embodiments, the bioresorbable polymer structure may be extruded or molded first, and then the antimicrobial agent may be deposited on the surface in liquid form by dipping, coating, or spraying. In some embodiments, the antimicrobial agent may be deposited by vapor deposition techniques known in the art (e.g. atomic layer deposition, plasma enhanced chemical vapor deposition, etc.). In some embodiments, the antimicrobial agents deposited on the surface of the bioresorbable polymer structure may be further coated with one or more additional bioresorbable polymers, such as poly(ethylene glycol) (PEG), to encapsulate the antimicrobial agent to slow the elution rate of the antimicrobial agent. In some embodiments, the additional bioresorbable polymer may be the same type of polymer making up the bioresorbable polymer structure. In other embodiments, the additional polymer may be a different type of polymer that than making up the bioresorbable polymer structure.

In some embodiments, the polymer device 36 may be formed by electro-spinning or electro-spraying the bioresorbable polymer as polymer fibers onto a cylindrical surface, such as an extrusion mandrel, to form a tubular shape, and then removing the polymer device 36 from the extrusion mandrel. The antimicrobial agent may be disposed within spaces formed by the electro-spun or electro-sprayed fibers by depositing solids, solutions, emulsions, or suspensions including the antimicrobial agent within the spaces. For example, solids may be deposited by plasma enhanced chemical vapor deposition, low pressure chemical vapor deposition, or atmospheric vapor deposition. In some embodiments, solutions, emulsions, and suspensions including the antimicrobial agent may be deposited by dipping, soaking, spraying, or spin coating. In some embodiments, the antimicrobial agent may be sprayed during the electro-spinning or electro-spraying process to entrap the antimicrobial agent.

In still other embodiments, the polymer device 36 may be formed by electro-spinning or electro-spraying the bioresorbable polymer as polymer fibers and the antimicrobial agent together onto a cylindrical surface, such as an extrusion mandrel, to form a tubular shape, and then removing the polymer device 36 from the extrusion mandrel. In some embodiments, the antimicrobial agent may be coaxially electro-spun or electro-sprayed along with the bioresorbable polymer. The antimicrobial agent may also be disposed within spaces formed by the electro-spun or electro-sprayed fibers by depositing solids, solutions, emulsions, or suspensions including the antimicrobial agent within the spaces. The elution rates of any antimicrobial agent disposed within the spaces may be controlled by controlling the spacing between the fibers, with greater spacing producing greater elution rates. The spacing between fibers may be controlled by adjusting process parameters of the electro-spinning or electro-spraying deposition process, such as solvent composition.

In the embodiment described above in reference to FIG. 2, a single polymer device 36 is described as wrapping around both leads 14, 16. However, it is understood that embodiments may include those in which the polymer device 36 wraps around only one of the leads 14, 16. In addition, embodiments may include a plurality of the polymer devices 36 in which each of the polymer devices 36 wraps around at least one of the leads 14, 16.

Figure 3:
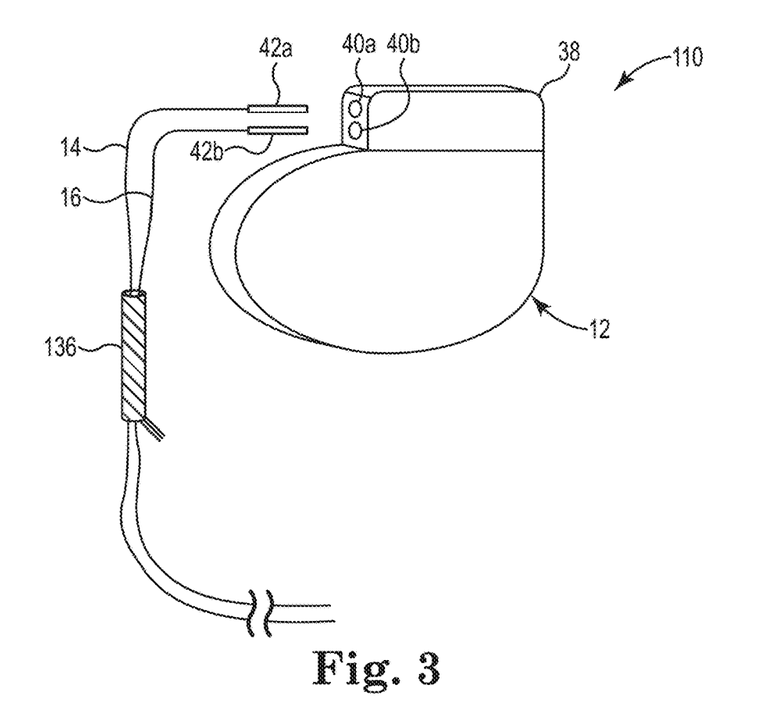
FIG. 3 is a schematic view of another implantable medical device including a polymer device in accordance with embodiments of the present invention.

FIG. 3 is a schematic view of another implantable medical device including a polymer device in accordance with embodiments of the present invention. FIG. 3 shows the IMD 110. The IMD 110 may be identical to the IMD 10 as describe above except that the IMD 110 includes a polymer device 136, instead of the polymer device 36. The polymer device 136 may be similar to the polymer device 36 described above, except that the polymer device 136 may be initially formed in a shape that is thin, long, and relatively narrow, such as the shape of a ribbon or a tape, and then wrapped around the leads 14, 16 to form the tubular shape that fits around the leads 14, 16 as they pass through the polymer device 136. In some embodiments, the polymer structure may be elastic and formed such that the polymer device 136 may be wrapped around the leads 14, 16 such that the polymer device 136 fits tightly around the leads 14, 16. With such a tight fit, the polymer device 136 is not likely to move along the leads 14, 16 without an effort by the surgeon to do so.

In some embodiments, the polymer device 136 may be formed by continuous, reel-to-reel electro-spinning or extrusion. In some embodiments, the polymer device 136 may be formed by batch processing on larger diameter drums and then cut to length. In some embodiments, the polymer device 136 may be supplied in rolls of between 12 and 18 inches in length.

Figure 4:
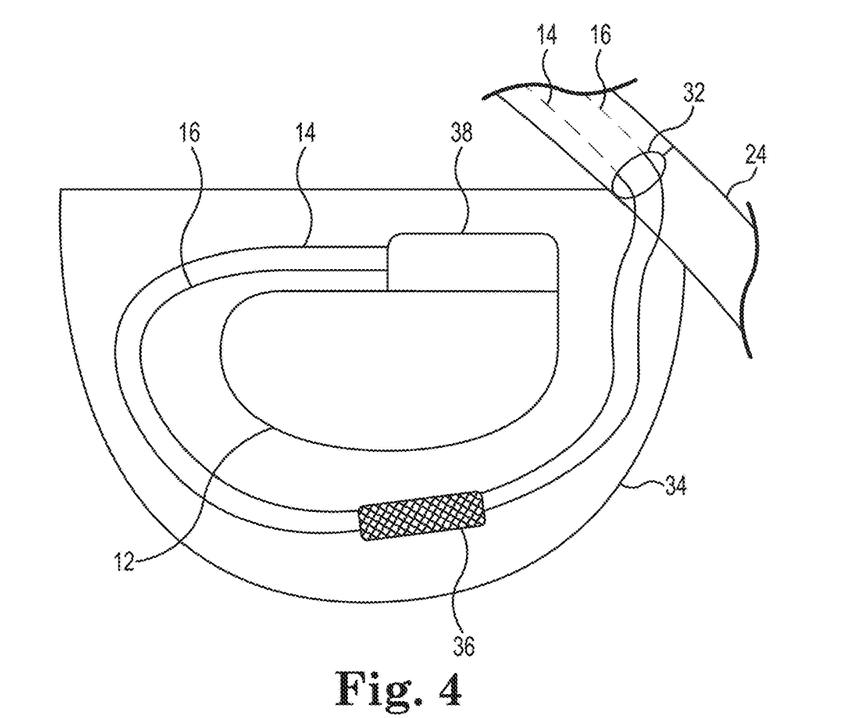
FIG. 4 is an enlarged schematic view of a portion of the implantable medical device including a polymer device of FIG. 1 subcutaneously implanted within a patient.

FIG. 4 is an enlarged schematic view of a portion of the IMD 10 including the polymer device 36 subcutaneously implanted within a patient as shown in FIG. 1. FIG. 4 shows the polymer device 36 fitted around the electrical leads 14, 16 within the subcutaneous pocket 34. The electrical leads 14, 16 enter the left auxiliary vein 24 through the vascular entry site 32. As shown in FIG. 4, the polymer device 36 does not cover any of a surface area of the housing 12. In other embodiments, the polymer device 36 may cover some of the surface area of the housing 12, for example, if the polymer device 36 is positioned adjacent to the housing 12 as the leads 14, 16 coil around the housing 12. However, in no embodiment does the polymer device 36 cover 20% or more of the surface area of the housing 12, as described below.

In operation, once the polymer device 36 is disposed within the subcutaneous pocket 34, the antimicrobial agent within may elute from the structure to prevent infection within the subcutaneous pocket 34. In some embodiments, the antimicrobial agent may elute relatively independently of the bioresorbtion of the structure of the polymer device 36. That is, the antimicrobial agent may elute completely out of the polymer device 36 before a significant portion of the structure of the polymer device is bioresorbed. In other embodiments, the antimicrobial agent may elute along with the bioresorbtion of the structure of the polymer device 36. In other embodiments, the elution of the antimicrobial agent may be a combination of elution independently of the bioresorbtion of the structure and elution along with the bioresorbtion of the structure.

The bioresorbtion of the structure of the polymer device 36 may result in nothing of the polymer device 36 being left behind after healing of the subcutaneous pocket 34 is complete. The polymer device 36 may not create any long-term discomfort or complications for the patient because it is completely bioresorbed, and thus eliminated from the patient's body.

As noted above, in some embodiments, the IMD 10 may require electrical grounding between the housing 12 and tissue surrounding the subcutaneous pocket 34 to successfully provide therapy. Any material or device covering a significant portion of the surface area of housing 12 may interfere with the electrical grounding of the IMD 10. This interference may be particularly troublesome should it change or drift in magnitude as the material or device covering the surface area of housing 12 changes, for example, by being bioresorbed. However, the bioresorbtion of the polymer device 36 may not create a troublesome change in the operation of the IMD 10 and its ability to provide therapy because it covers less than 20% of the surface area of the housing 12.

As described herein, the surface area of the housing 12 covered by the polymer device 36 is as implanted, at the time of implantation. The percentage area of the IMD 10 covered by the polymer device 36 may be determined by finding the area of housing 12 substantially in physical contact with the polymer device 36. The total area of the housing 12 is the total external surface area of the housing 12. The total area of the housing 12 may not include items connected to the housing 12, such as the header 38. The percentage area of the IMD 10 covered by the polymer device 36 may be the area of housing 12 substantially in physical contact with the polymer device 36, divided by the total area of the housing 12, with the resulting ratio expressed in percent.

In some embodiments, the polymer device 36 may cover less than 15%, less than 10%, less than 5%, or less than 1% of the surface area of the housing 12. In some embodiments, the polymer device 36 may not cover any of the surface area of the housing 12. By covering less than 20% of the surface area of the housing 12, the bioresorbtion of the polymer device 36 may not produce a change in the electrical grounding of the IMD 10 that is significant enough to interfere with the therapy provided by the IMD 10.

Figure 5:
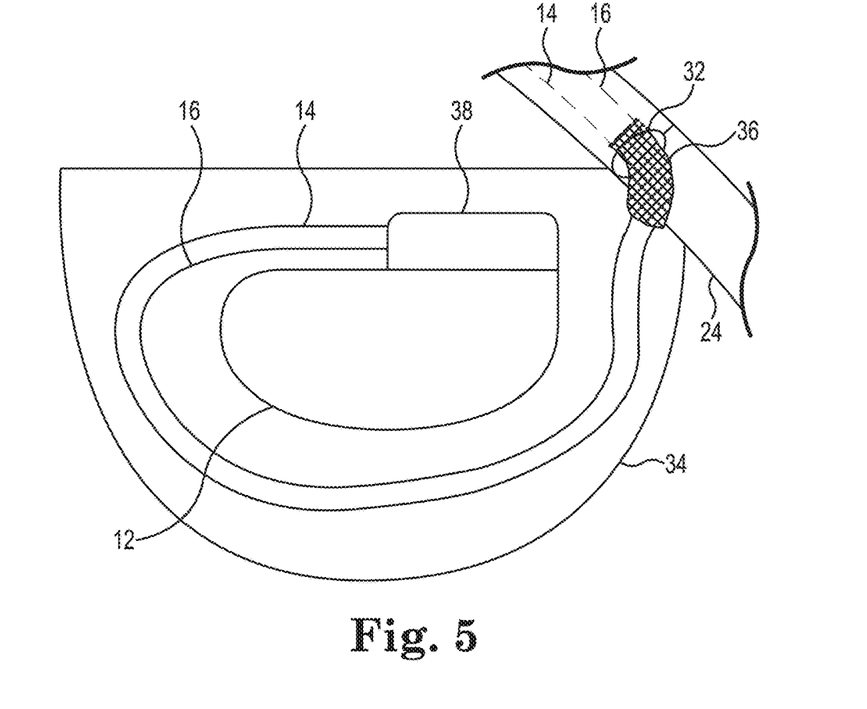
FIG. 5 is an enlarged schematic view of a portion of an implantable medical device and a polymer device subcutaneously implanted within a patient in accordance with embodiments of the present invention.

FIG. 5 is an enlarged schematic view of a portion of the IMD 10 in accordance with embodiments of the present invention, including the polymer device 36 fitted around the electrical leads 14, 16 within the subcutaneous pocket 34. The embodiment of FIG. 5 is identical to the embodiment of FIG. 4, except that a position of the polymer device 36 is adjusted along the electrical leads 14, 16 such that an end of the polymer device 36 is adjacent to or, as shown in FIG. 5, within the left auxiliary vein 24. In some embodiments, the polymer device 36 is at least substantially within the subcutaneous pocket 34. In some embodiments, "substantially" means that at least about 80% of the polymer device is within the subcutaneous pocket 34. In other embodiments, "substantially" means that at least about 85%, 90%, 95% or 99% of the polymer device 36 is within the subcutaneous pocket 34. In some embodiments, all of the polymer device 36 is completely within the subcutaneous pocket 34, and the end of the polymer device 36 is in physical contact with the left auxiliary vein 24 adjacent to the vascular entry site 32.

In operation, once the end of the polymer device 36 is adjacent to or within the left auxiliary vein 24, the antimicrobial agent within may elute from the structure to prevent any source of infection which might initially be found within the subcutaneous pocket 34 from entering the vascular system through the vascular entry site 32. Because the polymer device 36 is also substantially disposed within the subcutaneous pocket 34, the antimicrobial agent within may elute from the structure to prevent infection within the subcutaneous pocket 34.

Figure 6:
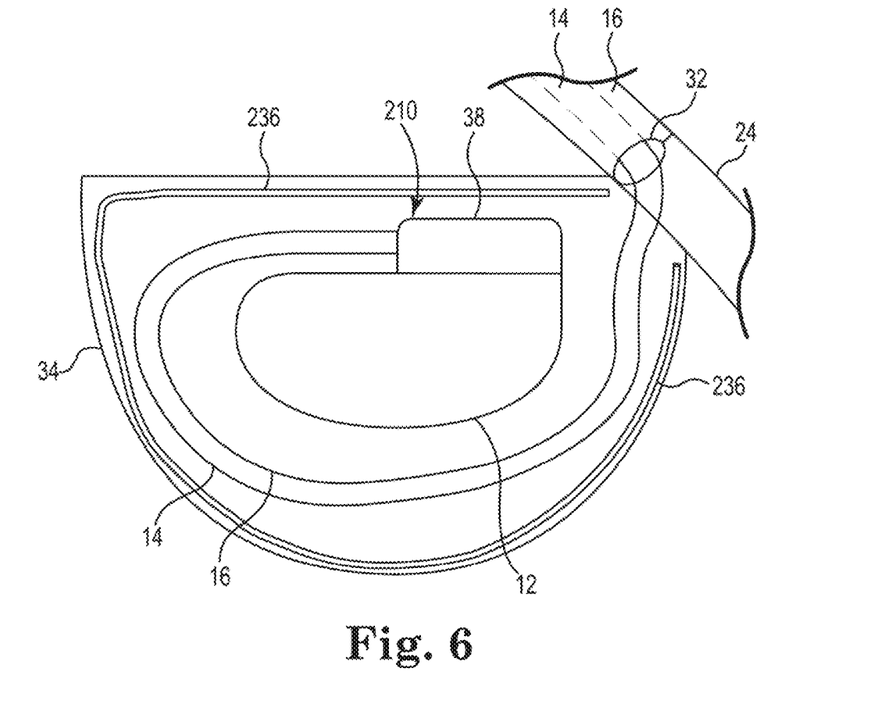
FIG. 6 is an enlarged schematic view of a portion of an implantable medical device and a polymer device subcutaneously implanted within a patient in accordance with embodiments of the present invention.

FIG. 6 is an enlarged schematic view of a portion of an implantable medical device and a polymer device subcutaneously implanted within a patient in accordance with embodiments of the present invention. FIG. 6 shows an IMD 210 implanted within a patient, as described above for IMD 10 in reference to FIG. 1. The IMD 210 is identical to IMD 10, except that it does not include the polymer device 36. The embodiment of FIG. 6 includes a polymer device 236. The polymer device 236 may be made of the same materials as the polymer device 36 described above, including a structure made of a bioresorbable polymer and an antimicrobial agent configured to elute from the structure. The polymer device 236 has an elongated shape. As shown in the embodiment in FIG. 6, the polymer device 236 may be in the form of a length of cord of woven polymer fibers. The polymer fibers may be formed by electro-spinning or electro-spraying. In other embodiments, the polymer device 236 may be in the form of an extruded length of polymer.

The polymer device 236 is configured to be implanted within the subcutaneous pocket 34 and is further configured to fit around a substantial portion of a perimeter of the subcutaneous pocket 34. As shown in FIG. 6, the polymer device 236 may fit around almost the entirety of the perimeter of the subcutaneous pocket 34. In some embodiments, a substantial portion may mean at least 50% of the length of the perimeter of the subcutaneous pocket 34. In other embodiments, a substantial portion may mean at least 60%, at least 70%, at least 80%, at least 90%, at least 95%, or 100% of the length of the perimeter of the subcutaneous pocket 34. In some embodiments, the polymer device 236 may be longer than the perimeter of the subcutaneous pocket 34 such that the polymer device 236 fits around 100% of the length of the perimeter of the subcutaneous pocket 34 and ends of the polymer device 236 overlap each other. In some embodiments, a surgeon may cut the polymer device 236 to a specific length to fit around the perimeter of the subcutaneous pocket 34 as desired. The ability of the surgeon to create a custom length of the polymer device 236 for a particular patient may lead to a more successful outcome in terms of infection prevention and patient comfort.

In operation, once the polymer device 236 is fitted around the substantial portion of the perimeter of the subcutaneous pocket 34, the antimicrobial agent within may elute from the structure to prevent infection within the subcutaneous pocket 34. As with the polymer device 36 described above, the bioresorbtion of the structure of the polymer device 236 may result in nothing of the polymer device 236 being left behind after healing of the subcutaneous pocket 34 is complete. That is, the polymer device 236 may be completely bioresorbable. The polymer device 236 may not create any long-term discomfort or complications for the patient because it is completely bioresorbed, and thus eliminated from the patient's body.

As with the polymer device 36, the polymer device 236 may cover less than 20% of the surface area of the housing 12. As described herein, the surface area of the housing 12 covered by the polymer device 236 is as implanted, at the time of implantation. In some embodiments, the polymer device 236 may cover less than 15%, less than 10%, less than 5%, or less than 1% of the surface area of the housing 12. In some embodiments, such as the embodiment shown in FIG. 6, the polymer device 236 may not cover any of the surface area of the housing 12. By covering less than 20% of the surface area of the housing 12, the bioresorbtion of the polymer device 236 may not produce a change in the electrical grounding of the IMD 210 that is significant enough to interfere with the therapy provided by the IMD 210.

The polymer device 236 may include a structure made of a bioresorbable polymer and an antimicrobial agent. In some embodiments, the bioresorbable polymer may include poly (lactic-co-glycolic) acid, polycaprolactone (PCL), poly-L-lactide (PLLA), or poly(lactide-co-glycolide)-block-poly (ethylene glycol) (PLGA-b-PEG), or any combination of the aforementioned polymers. In some embodiments, the polymer device 236 may be completely bioresorbable.

The antimicrobial agent may be configured to elute from the structure of the polymer device 236. In some embodiments, the antimicrobial agent may be disposed within the bioresorbable polymer. That is, the antimicrobial agent may be integrated into the bioresorbable polymer itself such that as the bioresorbable polymer is broken down, the antimicrobial agent may be released. For example, if the antimicrobial agent is a silver salt mixed into the bioresorbable polymer prior to forming the polymer device 236, silver ions may be released as the bioresorbable polymer is broken down. In some embodiments, the antimicrobial agent may include a silver salt, such as silver nitrate, or silver chloride. In other embodiments, the antimicrobial agent may include silver nanoparticles. In still other embodiments, the antimicrobial agent may include salts or nanoparticles of other metals having antimicrobial properties, such as gold or copper. In such embodiments, the antimicrobial agent may elute from the bioresorbable polymer device 236 as the bioresorbable polymer is bioresorbed.

In other embodiments, the structure of the polymer device 236 may include a plurality of fibers formed of the bioresorbable polymer. The antimicrobial agent may be disposed within spaces formed by the plurality of fibers. In such embodiments, the antimicrobial agent may be supplied as solids within the spaces, solutions within the spaces, emulsions within the spaces, or suspensions within the spaces. The antimicrobial agent may include any antibiotic or combination of antibiotics known in the art, for example, vancomycin, minocycline, gentamycin, or rifampin, or any of the antimicrobial agents described above. In some embodiments, the antimicrobial agent may elute from the spaces between the fibers substantially completely before the bioresorbable polymer device 236 is substantially bioresorbed. For example, the antimicrobial agent may elute substantially completely in a few days, whereas the bioresorbable polymer device 236 may not be substantially bioresorbed for several weeks. In other embodiments, the antimicrobial agent may elute from the spaces of the bioresorbable polymer device 236 in rough proportion to the bioresorbtion of the bioresorbable polymer device 236. For example, the antimicrobial agent may elute substantially completely in a few days, and the bioresorbable polymer device 236 may also be substantially bioresorbed in a few days.

In some embodiments, the polymer device 236 may be formed by extruding the bioresorbable polymer structure and the antimicrobial agent together to form an elongated shape. In other embodiments, the polymer device 236 may be formed by molding the bioresorbable polymer structure and the antimicrobial agent together to form an elongated shape. In other embodiments, the bioresorbable polymer structure may be extruded or molded first, and then the antimicrobial agent may be deposited on the surface in liquid form by dipping, coating, spraying. In some embodiments, the antimicrobial agent may be deposited by vapor deposition techniques known in the art (e.g. atomic layer deposition, plasma enhanced chemical vapor deposition, etc.). In some embodiments, the antimicrobial agents deposited on the surface of the bioresorbable polymer structure may be further coated with one or more additional bioresorbable polymers, such as poly(ethylene glycol) (PEG), to encapsulate the antimicrobial agent and enhance the elution properties. In some embodiments, the additional bioresorbable polymer may be the same type of polymer making up the bioresorbable polymer structure. In other embodiments, the additional polymer may be a different type of polymer that than making up the bioresorbable polymer structure.

In some embodiments, the polymer device 236 may be formed by electro-spinning or electro-spraying the bioresorbable polymer as polymer fibers, and then weaving the polymer fibers into a structure for the polymer device 236. The antimicrobial agent may be disposed within spaces formed by the electro-spun or electro-sprayed fibers by depositing solids, solutions, emulsions, or suspensions including the antimicrobial agent within the spaces. For example, solids may be deposited by plasma chemical vapor deposition, low pressure chemical vapor deposition, or atmospheric vapor deposition. Solutions, emulsions, and suspensions may be deposited by dipping soaking, spraying, or spin coating. In some embodiments, the antimicrobial agent may be sprayed during the electro-spinning or electro-spraying process to entrap the antimicrobial agent.

In still other embodiments, the polymer device 236 may be formed by electro-spinning or electro-spraying the bioresorbable polymer as polymer fibers and the antimicrobial agent together, and then weaving the polymer fibers into a structure for the polymer device 236. In some embodiments, the antimicrobial agent may be coaxially electro-spun or electro-sprayed along with the bioresorbable polymer. The antimicrobial agent may also be disposed within spaces formed by the electro-spun or electro-sprayed fibers by depositing solids, solutions, emulsions, or suspensions including the antimicrobial agent within the spaces. The elution rates of any antimicrobial agent disposed within the spaces may be controlled by controlling the spacing between the fibers, with greater spacing producing greater elution rates. The spacing between fibers may be controlled by adjusting process parameters of the electro-spinning or electro-spraying deposition process, such as solvent composition.

The embodiments above are described in the context of an exemplary implantable medical device in the form of a cardiac rhythm management system having a pulse generator and a pair of electrical leads. However, it is understood that embodiments may encompass other implantable medical devices, such as a drug delivery system having a drug pump and a catheter.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

EXAMPLES

The following Examples are illustrative and not intended to be limiting.

Bioresorbable Polymer Structure Preparation

A plurality of bioresorbable polymer structures were prepared by eletro-spinning poly(lactic-co-glycolic) acid (PLGA) dissolved in a solvent mixture of varying proportions of tetrohydrofuran (THF) and dimethyl formamide (DMF) onto a target surface. Varying the ratio of THF to DMF produced varying fiber sizes and varying spaces between the fibers. By controlling the spaces between the fibers, the elution rates of any antimicrobial agent subsequently incorporated into the spaces may be controlled.

Each sample was electro-spun with a 50% polymer to solvent mixture ratio on a mass/volume basis (e.g., 5 grams polymer dissolved in 10 ml solvent mixture is 50% mass/volume). The samples were spun in air having between 22-23% relative humidity at a temperature of 23° C. The dissolved polymer was electro-spun at a flow rate of about 0.3 ml/hour through a 22 gauge electro-spinning nozzle. The distance between the electro-spinning nozzle and the target surface was about 15 cm.

Figure 7:
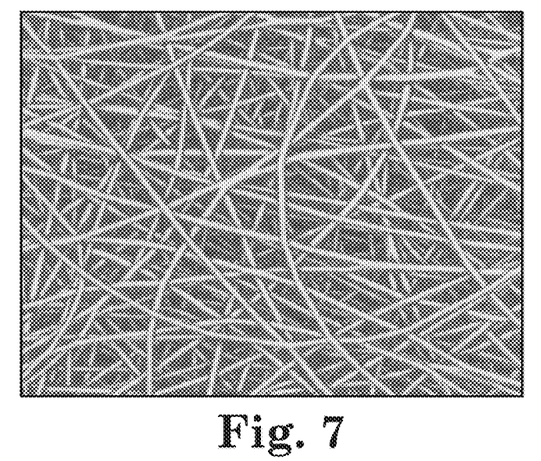
FIGS. 7-9 are photographs of a bioresorbable polymer structure formed by electro-spinning with various solvent mixtures.

FIG. 7 is a photograph of a bioresorbable polymer structure formed by electro-spinning as described above, with a solvent mixture of 2 parts THF to 1 part DMF. The structure is magnified by about 1000 times.

Figure 8:
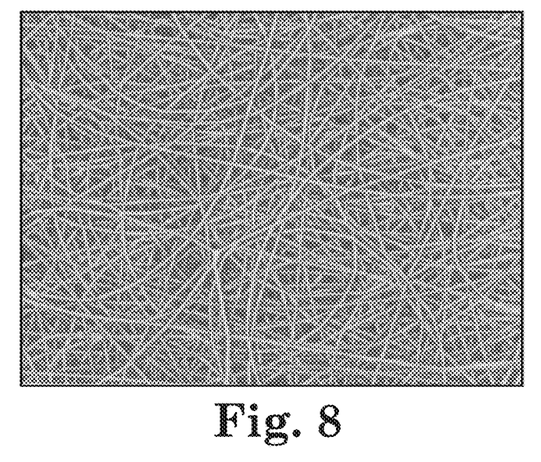

FIG. 8 is a photograph of a bioresorbable polymer structure formed by electro-spinning as described above, with a solvent mixture of 1 part THF to 1 part DMF. The structure is magnified by about 1000 times. The structure shown in FIG. 8 has smaller average fiber diameter and a smaller average space between fibers compared to the structure shown in FIG. 7.

Figure 9:
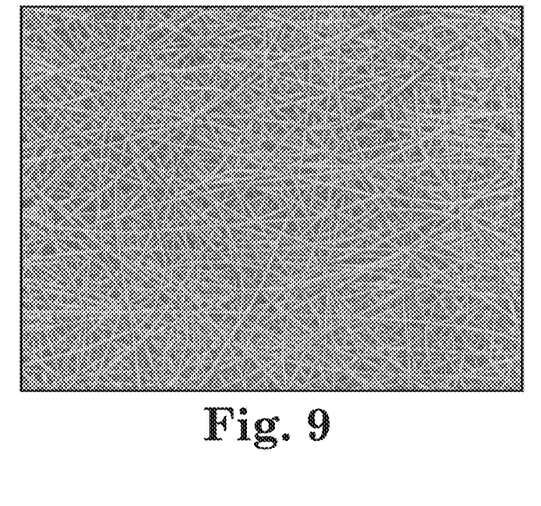

FIG. 9 is a photograph of a bioresorbable polymer structure formed by electro-spinning as described above, with a solvent mixture of 1 part THF to 2 parts DMF. The structure is magnified by about 1000 times. The structure shown in FIG. 9 has smaller average fiber diameter and a smaller average space between fibers compared to the structure shown in FIG. 8.

Thus, the average space between fibers may be controlled by varying the ratio of THF to DMF, with the average space between fibers decreasing as the ratio of THF to DMF decreases. In this way, elution rates of an antibiotic agent disposed within the spaces between fibers may also be controlled.

We claim:

1. A method of preventing infection resulting from implanting a medical device, the method comprising:
   installing a polymer device at least partially within a subcutaneous pocket formed to contain a housing of the medical device, the polymer device including a bioresorbable polymer structure and an antimicrobial agent configured to elute from the polymer structure; and
   installing the medical device housing in the subcutaneous pocket such that the polymer device covers less than 20% of the surface area of the medical device housing, wherein installing the polymer device includes:
      passing at least one electrical lead or at least one catheter through the polymer device;
      connecting the at least one electrical lead or the at least one catheter to the housing of the medical device such that the lead or catheter extends from the implantable medical device housing to a treatment site; and
      adjusting a position of the polymer device along the at least one electrical lead or at least one catheter such that an end of the polymer device is adjacent to or within a blood vessel through which the lead or catheter passes.

2. The method of claim 1, wherein the antimicrobial agent elutes from the polymer structure as the polymer structure is bioresorbed.

3. The method of claim 1, wherein the polymer device is formed as a polymer tape, and installing the polymer device includes:
   wrapping at least one electrical lead or at least one catheter with the polymer tape to form a tubular shape around the at least one electrical lead or at least one catheter.

4. The method of claim 1, wherein the antimicrobial agent is configured to elute from the bioresorbable polymer structure independently of the bioresorbtion of the bioresorbable polymer structure.

5. The method of claim 1, wherein the medical device is an implantable cardioverter-defibrillator.

6. A method of preventing infection resulting from implanting a medical device, the method comprising:
   implanting a polymer device at least partially within a subcutaneous pocket formed to contain a housing of the medical device, the polymer device including a bioresorbable polymer structure and an antimicrobial agent configured to elute from the polymer structure;
   implanting the medical device housing in the subcutaneous pocket, the medical device including at least one electrical lead or at least one catheter; and
   adjusting a position of the polymer device along the at least one electrical lead or at least one catheter such that an end of the polymer device is adjacent to or within a blood vessel through which the at least one electrical lead or at least one catheter passes.

7. The method of claim 6, wherein the end of the polymer device is within the blood vessel and polymer device is partially within the subcutaneous pocket.

8. The method of claim 6, wherein the end of the polymer device is within the blood vessel and at least 80% of the polymer device is within the subcutaneous pocket.

9. The method of claim 6, wherein the polymer device is entirely within the subcutaneous pocket and an end of the polymer device is adjacent to the blood vessel.

10. The method of claim 6, wherein implanting the polymer device further includes:
    passing at least one electrical lead or at least one catheter through the polymer device; and
    connecting the at least one electrical lead or the at least one catheter to the housing of the medical device such that the lead or catheter extends from the implantable medical device housing to a treatment site.

11. The method of claim 6, wherein implanting the polymer device further includes:
    wrapping at least one electrical lead or at least one catheter with the polymer tape to form a tubular shape around the at least one electrical lead or at least one catheter; and
    connecting the at least one electrical lead or the at least one catheter to the housing of the medical device so that the lead or catheter extends from the implantable medical device housing to a treatment site.

12. The method of claim 6, wherein the antimicrobial agent is configured to elute from the bioresorbable polymer structure independently of the bioresorbtion of the bioresorbable polymer structure.

13. The method of claim 6, wherein the antimicrobial agent is configured to elute along with the bioresorbtion of the bioresorbable polymer structure.

* * * * *